(12) United States Patent
Barlow et al.

(10) Patent No.: US 7,510,637 B2
(45) Date of Patent: Mar. 31, 2009

(54) MICROELECTRONIC ARRAYS FOR CELL-BASED FUNCTIONAL GENOMICS/HIGH THROUGHPUT PHENOTYPING BY ELECTROKINETIC ASSEMBLY

(75) Inventors: Carrolee Barlow, Del Mar, CA (US); Sangeeta N. Bhatia, La Jolla, CA (US); Mihrimah Ozkan, San Diego, CA (US); Sadik C. Esener, Solana Beach, CA (US)

(73) Assignees: The Regents of the University of California, Oakland, CA (US); The Salk Institute for Biological Studies, San Diego, CA (US)

( * ) Notice: Subject to any disclaimer, the term of this patent is extended or adjusted under 35 U.S.C. 154(b) by 685 days.

(21) Appl. No.: 10/450,085

(22) PCT Filed: Dec. 8, 2001

(86) PCT No.: PCT/US01/48263

§ 371 (c)(1),
(2), (4) Date: Dec. 15, 2003

(87) PCT Pub. No.: WO02/45835

PCT Pub. Date: Jun. 13, 2002

(65) Prior Publication Data

US 2005/0173249 A1 Aug. 11, 2005

Related U.S. Application Data

(60) Provisional application No. 60/254,416, filed on Dec. 8, 2000.

(51) Int. Cl.
*G01N 27/447* (2006.01)

(52) U.S. Cl. .................................. 204/450; 204/452

(58) Field of Classification Search ......... 204/450–455, 204/600–605
See application file for complete search history.

(56) References Cited

U.S. PATENT DOCUMENTS 4,661,451 A    4/1987    Hansen ...................... 435/174

(Continued)

OTHER PUBLICATIONS

S.N. Bhatia et al.; Effect of cell-cell interactions in preservation of cellular phenotype: cocultivation of hepatocytes and nonparenchymal cells; Nov. 1999; The Faseb Journal, pp. 1883-1990.

(Continued)

*Primary Examiner*—Alex Noguerola
(74) *Attorney, Agent, or Firm*—Gavrilovich Dodd & Lindsey LLP; Joseph R. Baker, Jr.

(57) ABSTRACT

An electrochemical apparatus 1 permits electric-field-assisted fluidic assembly of objects 2 on a patterned silicon substrate 11 by means of electrical addressing. Charged objects 2 such as beads and live cells are moved electrokinetically, like as in electrophoresis, through a solution, typically water 3, towards a micro-patterned charged semiconductor electrode, such as a silicon electrode 11 patterned with silicon dioxide, silicon nitride or agarose gel. The charged objects 2 are thus localized and assembled, most typically into arrays of multiple or single particles, in accordance with the patterning of the electrode 11. Correlating with theoretical predictions, negatively charged polystyrene beads of 20 μm diameter, or live mammalian cells of 20-30 μm diameter, can be assembled and disassembled on 100 μm feature size micro-patterned substrates by means of electrical addressing. The apparatus 1 has applications in creation of active cellular arrays for cell biology research, drug discovery and tissue engineering.

18 Claims, 5 Drawing Sheets

U.S. PATENT DOCUMENTS

| | | | | |
|---|---|---|---|---|
| 5,388,577 | A | * | 2/1995 | Hubbard ..................... 600/377 |
| 5,605,662 | A | * | 2/1997 | Heller et al. ............... 422/68.1 |
| 6,099,803 | A | | 8/2000 | Ackley et al. .............. 422/68.1 |
| 6,290,839 | B1 | | 9/2001 | Kayyem et al. .......... 205/777.5 |
| 6,605,453 | B2 | * | 8/2003 | Ozkan et al. ............. 435/173.1 |

OTHER PUBLICATIONS

Mark Chee et al.; Accessing Genetic Information with High-Density DNA Arrays; Oct. 25, 1996; Science, New Series, vol. 274, No. 5287, Genome Issue, pp. 610-614.

Christopher S. Chen et al.; Geometric Control of Cell Life and Death; May 30, 1997; Science, New Series, vol. 276, No. 5317, pp. 1425-1428.

Jing Cheng et al.; Preparation and hybridization analysis of DNA/RNA from *E. coli* on microfabricated bioelectronic chips; Jun. 16, 1998; Nature Biotechnology, vol. 16, No. 6, pp. 541-546.

Ravi Kapur, et al.; Streamlining the Drug Discovery Process by Integrating Miniaturization, High Throughput Screening, High Content Screening, and Automation on the CellChip™ System; Mar. 1999, Biomedical Microdevices, vol. 2, No. 2, pp. 99-109.

Gavin MacBeath, et al.; Printing Proteins as Microarrays for High-Throughput Function Determination; Sep. 8, 2000; Science, vol. 289, pp. 1760-1763.

Mihrimah Ozkan, et al.; Massively parallel low-cost pick- and-place of optoelectronic devices by electrochemical fluidic processing; Sep. 1, 2000; Optics Letters, vol. 25, No. 17, pp. 1285-1287.

Mihrimah Ozkan, et al.; Heterogeneous Integration through Electrokinetic Migration; Nov./Dec. 2001; IEEE Engineering in Medicine and Biology, pp. 144-151.

J.N. Turner, Ph.D., et al.; Biocompatibility of Microfabricated Neuroprosthetic Devices; Jun. 25-26, 2000; National Institutes of Health Bioengineering Consortium (BECON), pp. 33-34.

\* cited by examiner

MICROELECTRONIC ARRAYS FOR CELL-BASED FUNCTIONAL GENOMICS/HIGH THROUGHPUT PHENOTYPING BY ELECTROKINETIC ASSEMBLY

BACKGROUND TO THE APPLICATION

The present patent application is a 371 of PCT/US01/48263, filed on Dec. 08, 2001, descended from, and claims benefit of priority of, U.S. provisional patent application Ser. No. 60/254,416 filed on Dec. 8, 2000, having the same name, and to the same inventor, as the present patent application.

The invention of this disclosure was made by support of the U.S. Government under Grant No. MDA 972-98-1-0001 (SCE) acting through the United States Defense Advanced Projects Agency (DARPA). The U.S. Government has certain rights in this invention.

BACKGROUND OF THE INVENTION

1. Field of the Invention

The present invention generally concerns the organization and assembly of small objects including live cells by electrokinetic forces for purposes of cell-based biosensors, drug discovery, pharmacogenomics, functional genomics, high throughput phenotyping, and in-vitro biology (combinatorial cell culture, signal transduction mechanisms), tissue engineering or any application requiring massively parallel manipulation of small objects including biological cells.

The present invention particularly concerns an apparatus and method for the assembly and disassembly of small objects including live mammalian cells by movement of these objects electrokinetically, like as in electrophoresis, through a solution, typically water, towards a micro-patterned charged semiconductor electrode, such as a silicon electrode patterned with silicon dioxide, silicon nitride or agarose gel.

2. Description of the Prior Art

Existing cell arraying technologies primarily rely on patterned surface chemistries or localization through polymeric templates.

Meanwhile, and on another topic, cells including live cells are responsive to an electric field. Cells are negatively charged due to sialic acid residues in their glaycocalix. They will thus move toward a positive pole in the presence of an electric field.

SUMMARY OF THE INVENTION

The present invention contemplates the patterning, arraying, and assembly of small objects including microorganisms (such as bacteria) and biological cells (such as mammalian and plant cells) by use of electrokinetic forces in an electrokinetic apparatus and within an electrochemical system, and certain uses of the arrays of small objects so formed.

1. The Invention, and Its Function

The apparatus of present invention is suitable to manipulate small things upon which an electrical charge is present, or may be placed. Cells are negatively charged due to sialic acid residues in their glaycocalix, and will tend to move towards a positively charged electrode when suspended in a solution.

In the apparatus and method of the present invention an electrochemical system consisting of two parallel plates is used to transport charged objects in solution. One of the parallel plates—the anode (i.e., the positive plate) when the objects are negatively charged—is a dielectric-patterned semiconductor substrate. The patterning may be realized with silicon dioxide, silicon nitride or, preferably in cell assembly applications, agarose gel. The other, cathode (i.e., negative), plate is also a semiconductor, and preferably one that is transparent so as to permit in-situ observations of the charged objects and their movements.

When an electric field is applied between the electrodes an $H^+$ and $OH^-$ ion exchange occurs between two electrodes occurs as a result of the reduction and oxidation (REDOX) of water ions. The circulation of these ions results in completion of the electrical circuit within the apparatus.

However, because of the patterning of one electrode (the anode) this REDOX is not uniform over the area of the electrode and the volume of the apparatus. If, for example, a silicon substrate is patterned with silicon nitride, the current density will be highest near to the silicon and less where the silicon nitride is patterned. The charged objects will move under electrokinetic forces of this unequal current distribution, and electric field. Other fluidic forces including electrophoretic, electrohydrodynamic and/or electrosmotic forces are, or may be, also involved. However, the objects may be aligned, typically with massive parallelism, in accordance with the patterning.

Furthermore, a mathematical model of these forces—validated in actual operation and observation—predicts that the voltage required for the disassembly of small objects—such as, for example, identical spherical polystyrene beads—is substantially higher than the voltage required for assembly. The difference arises due to the combined effects of gravity, frictional drag and van der Waals forces. The apparatus can thus be used to good effect for, for inter alia, the patterning of live mammalian cells by using low conductance physiologic buffers. The cells—such as, for example mouse 3T3 fibroblast cells—maintain the ability to attach, spread and divide after exposure of up to 100 V/cm. Accordingly, the apparatus and method of the invention accord a powerful tool for high throughput biological screening.

2. Uses of the Present Invention

The method and apparatus of the invention are suitable for cell-based functional genomics and high throughput phenotyping applications including the following:

Libraries of, for example, live single cells used in, for example, functional clonal assays may be rapidly and simultaneously arrayed by electrical forces in any desired format without use of hostile cell sorting procedures.

Live cells may be monitored in real time, and in parallel, for functional conditions (e.g., mitosis, migration, or morphology), for fluorescent light emission, or for still other signals. The method and apparatus of the invention support the variety of "readout" mechanisms based on transcriptional activity of single cells that have been proposed by C. Barlow, and which are explained in this specification.

The present invention supports, and is fully compatible with, selection of individual cells or cell clones using mechanical (e.g., tweezers), fluidic (e.g., a syringe), electronic (e.g., a probe), or optical (e.g., optical tweezers) techniques to remove, retain, or capture cells or the like for further testing.

The present invention supports development of a neural progenitor cell library with random integration of a reporter gene throughout the genome (gene trapping) in order to identify genes that are differentially regulated after exposure to various compounds.

The technology of the present invention supports manipulation of a) cell libraries generated using a variety of approaches, b) libraries of different fluorescent fusion proteins, c) libraries of randomly integrated reporter constructs and d) libraries of random-activated genes.

3. Advantages of the Present Invention

In the apparatus and method of the present invention cells and like small objects may be rapidly arrayed in massive parallelism. This arraying is based on charge and not on any receptor mediated adhesion.

By appropriately sizing and shaping the patterned regions as small circular dots, arrays of but one single cell per dot may readily be obtained.

Monitoring of all arraying activity may be readily realized by simple visual observation in real time.

Individual cells may be picked and placed anywhere within the array by conventional mechanisms for so doing, including optical tweezers.

The apparatus is low in cost, and can readily be fabricated on various types of substrates including silicon, polymer, and glass which may be variously transparent and/or flexible/

The apparatus permits of the selective capture of cells (or other small objects) of interest in accordance with their variable properties as relate to their responses to the electrokinetic forces of the apparatus.

The apparatus and method of the present invention are less hostile than other tools to cells in the formation of single cell clones, e.g., FACS.

The apparatus and method of the present invention are fully integratable with both (i) microfluidics and (ii) optical control.

4. An Electrochemical Apparatus

Therefore, in one of its aspects the present invention is embodied in an electrochemical apparatus having electrodes separated by a fluid.

Within the electrochemical apparatus at least one electrode is patterned with insulator so as to leave patterned conducting regions of small size. By this construction if (i) small objects of a size commensurate to the patterned conducting regions are (ii) entered into the fluid, and (iii) an electrical is applied between the electrodes, then the small particles will be caused by electrokinetic forces to migrate in the fluid to the conducting regions so as to assume the spatial pattern thereof. (The "electrokinetic forces" are similar to electrophoretic forces.)

In the apparatus the patterned electrode is preferably made of semiconductor patterned with an insulator, but may alternatively be a conductor patterned with an insulator. If a semiconductor, the electrode is preferably of material drawn from the group consisting essentially of silicon and indium tin oxide, and is more preferably silicon. The insulator is then preferably drawn from the group consisting essentially of silicon oxide, silicon nitride, agarose gel, and non-adhesive polymers, and is most commonly silicon nitride. If the electrode is a conductor, it is preferably a metal, and more preferably gold or silver. The insulator is then preferably drawn from the group consisting essentially of agarose, polymer, and polydimethylsiloxane (PDMS).

A practitioner of the electrochemical and/or the electrical materials arts will recognize these, and other, components to be suitable, and to be suitably substituted, one insulator for another, one semiconductor for another, etc. For example, a semiconductor electrode can be patterned with polymer.

In one preferred embodiment of the electrochemical apparatus the patterned electrode is nonadhesive, and is typically agarose.

The patterned electrode is most typically the anode, especially when the apparatus is used with animal or plant cells.

Most typically only one electrode is patterned. The other electrode is preferably transparent. A transparent electrode is preferably made from indium tin oxide (ITO).

The patterned electrode is preferably so patterned in a regular array, more preferably with regions suitably sized so as to capture, from a solution containing cells when an electrical potential is applied between the electrodes, either (i) multiple, or (ii) one, cell(s) each region.

The patterned electrode is normally patterned with regions of size less than or equal to 100 µm.

The electrochemical apparatus is suitably operated by configuration of each of its patterned electrode, the separating fluid, and the applied voltage potential, so as to pattern living cells.

5. An Electrochemical System

In another of its aspects the present invention is embodied in an electrochemical system having (i) an electrochemical apparatus, having two electrodes at least one of which is patterned with insulator so as to leave patterned conducting regions of small size, that holds between its two electrodes (ii) a fluid containing (iii) small objects of a size commensurate to the patterned conducting regions. When (iv) an electrical potential is applied between the electrodes the small objects in the fluid will be caused by electrokinetic forces to migrate to the conducting regions of the at least one electrode so as to assume the spatial pattern thereof.

The at least one patterned electrode of the electrochemical apparatus is preferably a semiconductor patterned with insulator, the fluid is preferably water, and the objects of a size commensurate to the patterned conducting regions are most commonly animal or plant cells, including mammalian cells.

The electrochemical system is effective to pattern cells, including as are living.

6. A Method of Patterning Small Objects

In yet another of its aspects the present invention is embodied in a method of patterning small objects.

In the method small objects within a fluid within an electrochemical apparatus that has electrodes separated by the fluid—one of the electrodes being patterned with insulator so as to leave patterned conducting regions of small size commensurate with the size of the small objects—will—when a suitable electrical potential is established between the electrodes—migrate in the fluid, and between the electrodes, under electrokinetic force so as to assume the spatial pattern of the conducting regions.

The patterned objects are preferably cells, which may be live.

The cells may patterned into single cell islands, and are preferably so patterned when the patterning method is expanded into an assay method also in accordance with the present invention. In the preferred embodiment of the assay method (i) a soluble stimulus is introduced to the cells that are patterned into single cell islands, and (ii) cellular response is observed.

The soluble stimulus may be, for example, a hormone or other cell differentiator.

In assay method a fluorescent reporter is commonly introduced to the cells so as to be used to visualize cellular response in presence of the stimulus. This observed response may be, by way of example, indicative of gene expression. This response is preferably so observed dynamically and in real time as the cells respond to the stimulus.

These and other aspects and attributes of the present invention will become increasingly clear upon reference to the following drawings and accompanying specification.

BRIEF DESCRIPTION OF THE DRAWINGS

Referring particularly to the drawings for the purpose of illustration only and not to limit the scope of the invention in any way, these illustrations follow:

FIG. 5, consisting of FIGS. 5a and 5b, illustrate the forces on a sphere inside a bulk solution (e.g. during assembly with the apparatus of the present invention shown in FIG. 1.

FIG. 6, consisting of FIGS. 6a and 6b, show the results of patterning 20 μm diameter polystyrene spheres in deionized water; FIG. 6a showing that the microspheres were patterned within the dot areas of the electrode of the apparatus previously seen in FIG. 1 when a positive bias is applied while

FIG. 7, consisting of FIGS. 7a and 7b, illustrates the general scheme for gene trapping; FIG. 7a showing the components of a gene trapping system including the promoter, exons and introns while

DESCRIPTION OF THE PREFERRED EMBODIMENT

Figure 1:
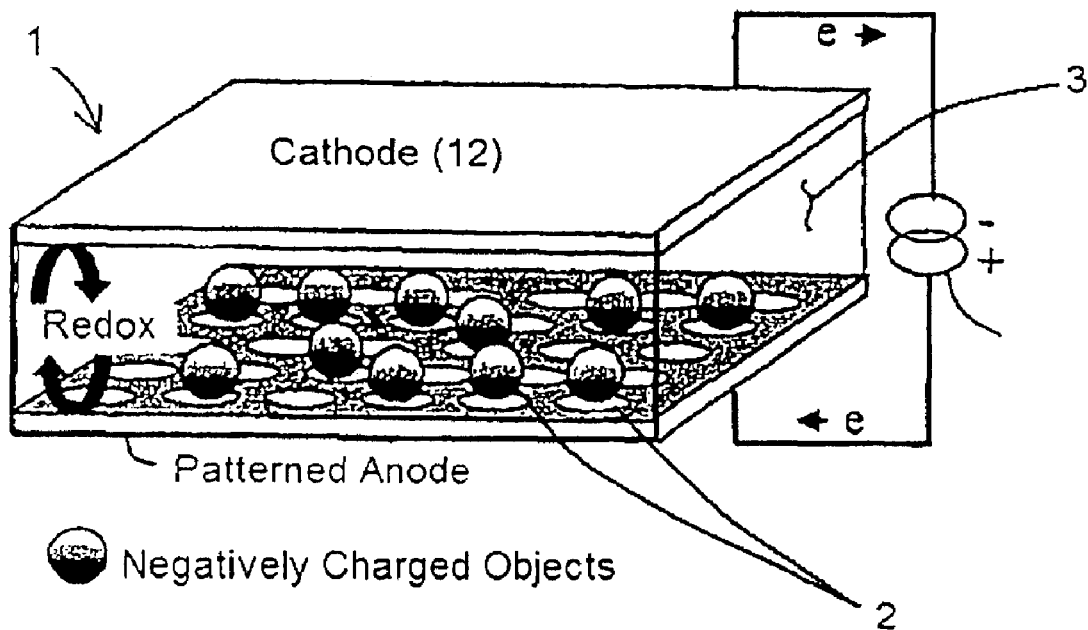
FIG. 1 is a schematic illustration of the electrochemical system of the present invention using a micro-patterned electrode in an electrokinetic apparatus.

The following description is of the best mode presently contemplated for the carrying out of the invention. This description is made for the purpose of illustrating the general principles of the invention, and is not to be taken in a limiting sense. The scope of the invention is best determined by reference to the appended claims.

Although specific embodiments of the invention will now be described with reference to the drawings, it should be understood that such embodiments are by way of example only and are merely illustrative of but a small number of the many possible specific embodiments to which the principles of the invention may be applied. Various changes and modifications obvious to one skilled in the art to which the invention pertains are deemed to be within the spirit, scope and contemplation of the invention as further defined in the appended claims.

In the preferred embodiment of an electrochemical system and apparatus of the present invention the fluidic assembly of objects on a micro-patterned silicon substrate is realized by means of electrical addressing. The assembly is based on the principle that charged species in solution will move to an oppositely charged electrodes, as seen commonly in electrophoresis. In the preferred embodiment of the apparatus of the invention charged species such as beads and cells are moved electrokinetically through an aqueous solution towards a charged electrode. Micro patterning of the electrodes permits localization of these charged species.

Furthermore, a theoretical framework predicts the electric potential for assembly and disassembly of spherical objects. These theoretical predictions have been found to correlate well with the observed motion and assembly of negatively-charged polystyrene beads of 20 μm diameter on 100 μm feature sized micro-patterned substrates. These results have been further extended to the arraying of 20-30 μm diameter live mammalian cells by means of electrical addressing.

This technique has applications in creation of "active" cellular arrays for cell biology research, drug discovery and tissue engineering.

1. Processes Relevant to the Invention

The potential synergy of combining MEMS (micro-electro-mechanical systems) with biological systems has become increasingly apparent in recent years. Already, the interface between biology and micro technology has led to the development of enabling tools for biological research clinical diagnostics, and medical devices. See Turner, J. N., Shain, W., Szaraski, D. H., Sopple, B., Lasek, S., Spence, A., Isaacson M. and Craighead H., "Biocompatibilty of micro fabricated neuroprosthetic devices"; Nanoscience and Nanotechnology, NIH conference; June 2000; Maryland. See also Chen, C. S., Mrksich, M., Huang, S., Whitesides, G. M., and Ingber, D. E., Science 276; 1425-1428; 1997.

At the "chip" level, this confluence of technologies has led to DNA microarrays. See Chee, M., Yang, R., Hubbell, E., Berno, A., Huang, X. C., Stern, D., Winkler, I., Lockhart, D. J., Morris, M. S., and Fodor, S. P. A., "Accessing genetic information with high-density DNA arrays", Science 274; 610-614, 1996.

It has led to catalytic RNA arrays. See Jing Cheng, et. al., "Preparation and hybridization analysis of DNA/RNA from E. calf on microfabricated bioelectronic chips" Nature, Vol. 16, (No. 6), June 1998, pp. 541-746.

It has led to protein arrays. See MacBeath, G., and Screiber, S. L., "Printing proteins as microarrays for high-throughput function determination", Science, vol. 289, 2000.

It has even led to live cell arrays. See Kapur. R., Giuliano, K. A., Campana. N. I. Adams, T., Olson. K., Jung. D., Mrksich, M., Vasudevan, C., and Taylor, L., "Streamlining the drug discovery process by integrating miniaturization, high throughput screening, high content screening and automation on the cell chip system", Biomedical microdevices, 2:2. 99-109, 1999. See also Bhatia, S. N., Balis, U. J., Yarmush, M. L., and Toner, M., "Effect of cell-cell interactions in preservation of cellular phenotype cultivation of hepatocytes and nonparenchymal cells", Faseb. 1883-1900, vol. 13, 1999. See also Chen, et al., op cit.

Cell arraying technology has proven to be a useful tool for studies of cell fate, cell-cell interaction, and cell-matrix interactions. Furthermore, some investigators have proposed the use of live cells as "high content sensors" for biological events. See Kappur, et al., op cit.

Existing cell arraying technologies primarily rely on patterned surface chemistries or localization, through polymeric templates. However, the process of cell arraying due to cell adhesion requires on the order of 2-12 hours.

2. The Method and Apparatus of the Invention

The method of the present invention is based on rapidly arraying live cells based on their negative charge rather than relying on receptor-mediated adhesion.

The method and apparatus of the invention may be demonstrated, and most clearly seen, by manipulation of polystyrene beads as model "cells", but the invention is fully extendable to cell lines of human and plant origin.

The preferred embodiment of an electronic and electrochemical apparatus 1 in accordance with the present invention in use for dynamic, reversible assembly of organic objects is shown in FIG. 1. The apparatus 1 is used to transport and to array charged species, or particles, or objects 2 present in a solution 3. The arraying is in accordance with the patterning of one substrate—normally the anode 11. An electric field is created between this anode 11 and a spaced-parallel electrode 12—the cathode 12—by an external power, or current, source 4. The closed loop current path is enabled by the reduction and oxidation—Redox—of water ions. The objects 2 become charged.

The substrate electrodes 11, 12 are preferably fabricated as anodic substrates. Preferably, a 400 nm thick silicon nitride dielectric layer is first deposited on a silicon wafer by using plasma enhanced chemical vapor deposition technique. Then, 100 μm diameter spots, here in the form of a regular two-dimensional array, are defined in the anode 11, preferably by process of photolithography. Finally, the nitride layer is etched away within each 100 μm diameter spot, preferably by $CF_4$ plasma. With this electrode configuration, the silicon electrode is in contact with electrolyte solution only at the 100 μm diameter openings.

The negatively charged objects 2 may be microspheres, live cells or the like. The solution 3 is preferably water. The cathode 12 is preferably transparent, and is more preferably made from Indium Tin Oxide (ITO).

Figure 2:
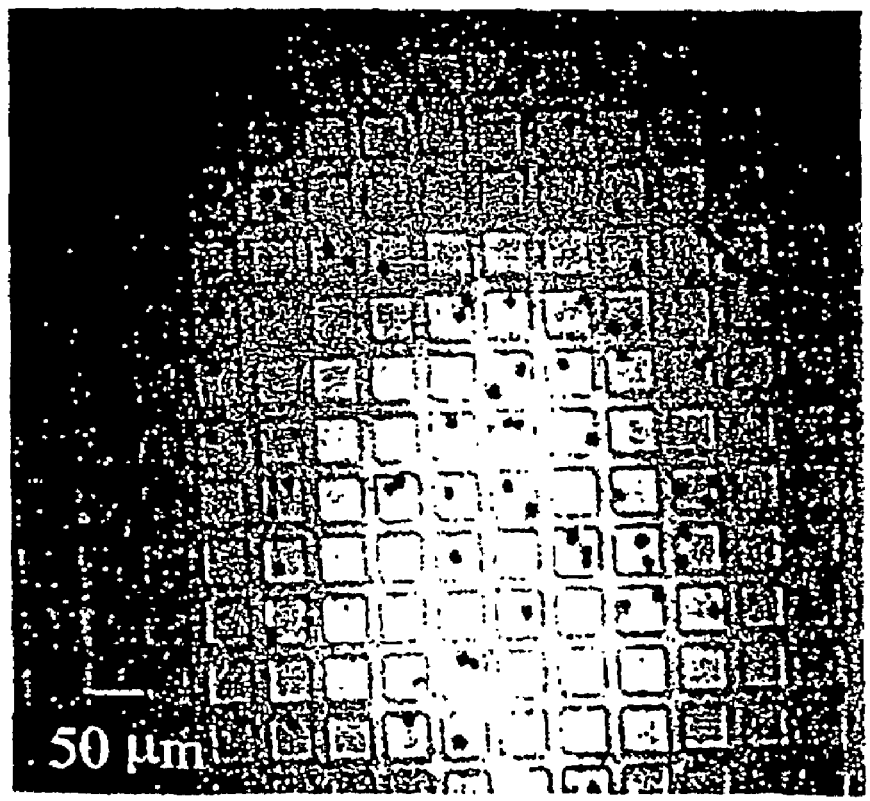
FIG. 2 shows an array of variable numbers of multiple small objects—mouse fibroblasts—at each location, or die, or pad of a regular array of such locations, dice, or pads located upon an electrode.

Mouse fibroblast cells as are assembled on patterned 50×50 micron size square pads are shown in FIG. 2. Various numbers of cells have been assembled on each pad, some pads holding multiple cells.

Figure 3:
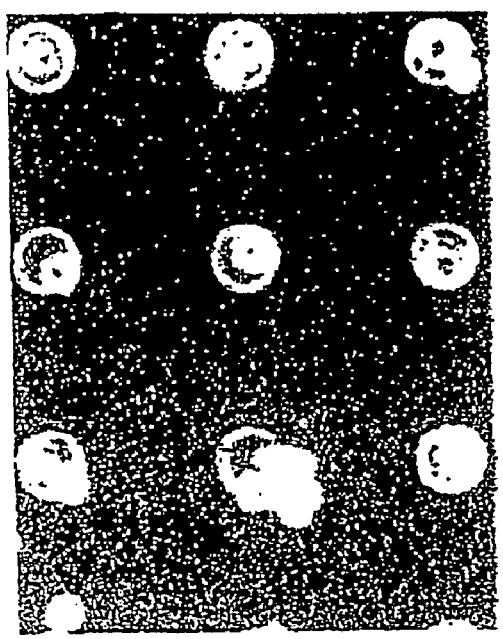
FIG. 3 shows an array of a single small object—a neuronal cell—at each location, or die, or pad of a regular array of such locations, dice, or pads located upon an electrode.

An array of, by way of example, single neuronal stem cells assembled on 20 mm diameter ITO electrodes situated between patterned agarose gel is shown in FIG. 3. The cells are of such size relative to the patterned areas, or pads, that only one cell fits on each pad.

It is possible to view fluorescent light, serving as a "readout" from objects, normally cells, assembled in and by the micro arraying apparatus of the present invention. In such a case the cells can show up brilliantly and distinctly, and at differing colors such as green and red as reflect different cells or cell conditions. In other words, the arrayed objects (the cells) are much more distinctly visible than in FIGS. 2 and 3. Alas, the drawings do not emit light, and are not even printed in color, leaving it to the able imagination of the reader to visualize that the manipulated objects can be, and commonly are, highly visible and distinct through the transparent cathode 12 (seen in FIG. 1). It is thus of course possible to view the assembly activity of the electrokinetic device in real time as it transpires.

Furthermore, it will be understood that individual objects—commonly individual cells—and be manipulated and transported by optical beams passed through the transparent cathode 12 (seen in FIG. 1). The most common technique is the well known optical tweezers. When this optical tweezing transpires a single object, or cell, may be observed to move, others remaining stationary.

3. Theory, Use and Results of the Apparatus of the Invention

The apparatus 1 of the invention—consisting essentially only of two parallel plates—has—when enabled as a full electrochemical system by the presence of the charged objects 2, solution 3 and current source 4—been used to transport the objects 2, which become charged, in the solution 3 (all seen in FIG. 1). A dielectric (silicon dioxide or silicon nitride) patterned semiconductor substrate has been fabricated and is used as anode. Another transparent semiconductor is used as cathode to enable in-situ observations.

See, as background to the construction of similar apparatus and electrochemical systems, Ozkan. M., Ozkan, C., Kibar. O., Wang. M., Bhatia, S., and Esener, S., "Heterogeneous Integration of Biological Species and Inorganic Objects by Electrokinetic Movement", IEEE Journal of EMB Magazine, in press. See also Ozkan, M., Kibar, O., Ozkan, C., and Esener, S. "Massively parallel low cost pick and place of optoelectronic devices via electrochemical fluidic processing", Optical Letters, September 2000.

In the schematic illustration of the electrochemical system of the invention shown in FIG. 1 the spheres represent negatively charged objects 2 inside the electrolyte solution. $H^2$ and $OH^-$ ion exchange between the two electrodes 11, 12 occurs as a result of the reduction and oxidation (REDOX) of water ions (of the water solution 3) under the applied electrical bias of the power, or current, source 4. The circulation of ions results in completion of the electrical circuit within the system.

Figure 4:
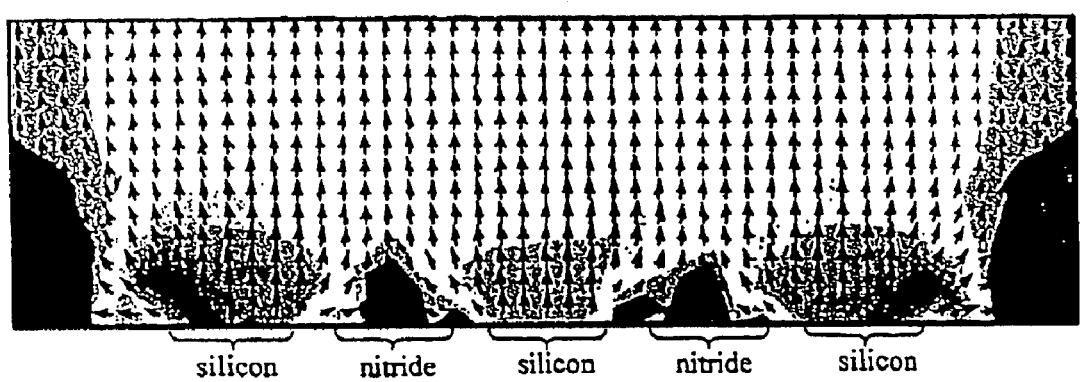
FIG. 4 is a 2-D finite element model of the current density distribution for the micro-patterned electrode at an applied potential of 3 V.

A two-dimensional (2-D) finite element model of the current density distribution inside the apparatus 1 in operation as an electrochemical system is shown in FIG. 4. Arrows show the direction of the electric field. The voltage applied by the poser source 4 (shown in FIG. 1) is nominally 3V. The electrokinetic apparatus, or cell, 1 is of composition silicon anode 11 patterned with silicon nitride, water as the solution 2, and ITO as the anode 12 (not shown in FIG. 4, shown in FIG. 1). Notice the non-uniform field distribution in comparison to regular micro-patterned electrode configuration. As expected, current density is larger over the electrode surface then elsewhere. Furthermore, the current density at the silicon-nitride interface is found to be highest near to the center of the patterned silicon dots, and lowest outside these dots where the electrode is still covered with silicon nitride.

Figure 5A:
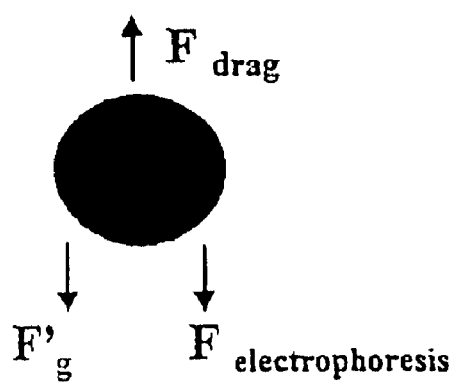
FIG. 5a shows the forces when the sphere is distant from the electrode surface (e.g., during assembly) while FIG. 5b shows the forces when the sphere is proximate to the electrode surface (e.g., during disassembly).
Figure 5B:
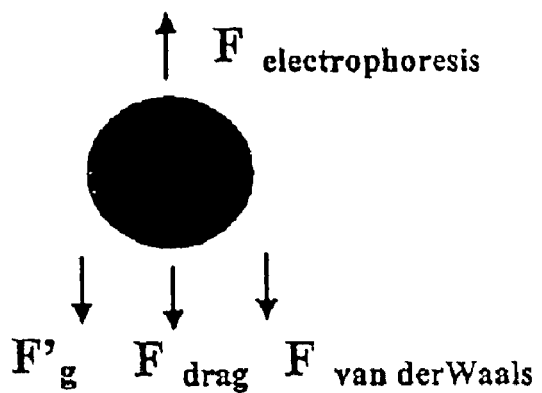
FIG. 5, consisting of FIGS. 5a and 5b, show the forces acting on a sphere when the sphere is respectively (a) inside the bulk solution, and (b) near to the electrode surface in the chamber of the electrokinetic apparatus of the present invention previously seen in FIG. 1.

4. Force Balance on Objects Assembled (Patterned) by the Electrokinetic Apparatus in the Electrochemical System of the Invention The required minimum bias to pattern objects under an applied electric field in a fluidic environment depends on the total forces acting on object. Hence it is important to understand forces acting on the cells inside the electrolyte when a bias is applied. The forces on the sphere inside the bulk solution (e.g. during assembly) are shown in FIG. 5a. The forces when the sphere is near the electrode surface (e.g., during disassembly) are shown in FIG. 5b. Note the inclusion of surface interactions in the latter Figure.

The following equation (1) gives the individual forces and their definitions when the object is transported down to the anode 11:

$$F_{drag} = F_g + F_{electrophoresis} \qquad (1)$$

where $$F_{drag} = 6\pi\eta Rv$$

is the fluidic drag force acting on a sphere.

The resultant force acting on a sphere due to gravitational and buoyancy forces is:

$$F'_g = F_g + F_b = V(\rho_p \rho_1)g$$

and $$F_{electrophoresis} = -q\frac{dV}{dx}$$

is the electrophoretic force acting on the object.

Following equation (2) represents the forces acting on the sphere when it is near to the electrode surface.

$$F_{drag}+F'_g+F_{vanderWaals}=F_{electrophoresis} \quad (2)$$

where $F_{vanderWaals}$ is the van der Waals force present between electrode and object. The Van der Waals force is inversely proportional to the seventh power of spacing between object and electrode surface. In order to dislodge the object from the electrode surface the applied bias has to overcome the sum of opposite forces acting on object.

In experiments test the above-stated mathematical predictions an applied repulsive potential necessary to prevent the sedimentation of a given sphere was applied. Polystyrene spheres of 20 μm diameter were used as models for plant and animal cells. Solution of equation (1) indicates about 0.75 mV/mm of electric field acting in an opposite direction is needed to balance the forces acting on the sphere when the sphere moves with the speed of $10^{-4}$ cm/s. Otherwise the sphere will sediment in de-ionized water, since the density of polystyrene is 1.05 g/cc.

This behavior correlates with experimental observations for the object velocity of the same order of magnitude. On the other hand, in order to reject the pre-patterned sphere from the electrode surface, the applied electric field has to overcome all the other existing forces on the sphere as shown in FIG. 3b. The required electric field to dislodge a 20 μm diameter polystyrene sphere in de-ionized water is calculated to be approximately 4 V/mm when the sphere is about 100 nm away from the electrode surface—Experimental observations have shown that spheres are dislodged with as little as 2 V/mm. This difference could be due to variations in the spacing between the sphere and electrode surface or other fluidic forces acting on the sphere (e.g. electrohydrodynamic or electrosmotic forces).

5. Assembling (Patterning) Objects with the Electrokinetic Apparatus and Electrochemical System of the Invention Actual experimental data is given on microspheres as typical, and illustrative, of the small objects 2 (shown in FIG. 1) successfully assembled (i.e., patterned) with the electrokinetic apparatus and electrochemical system of the present invention.

Figure 6A:
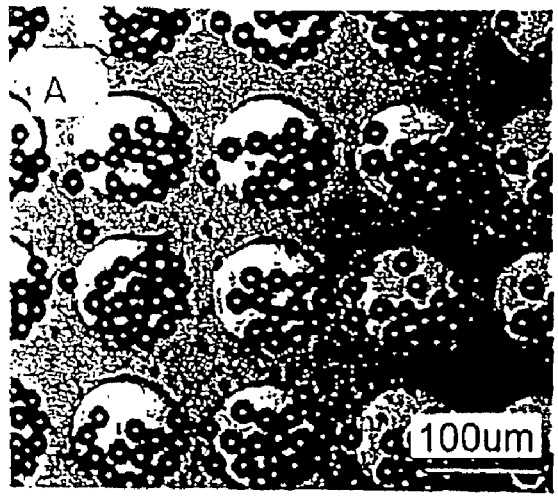
Figure 6B:
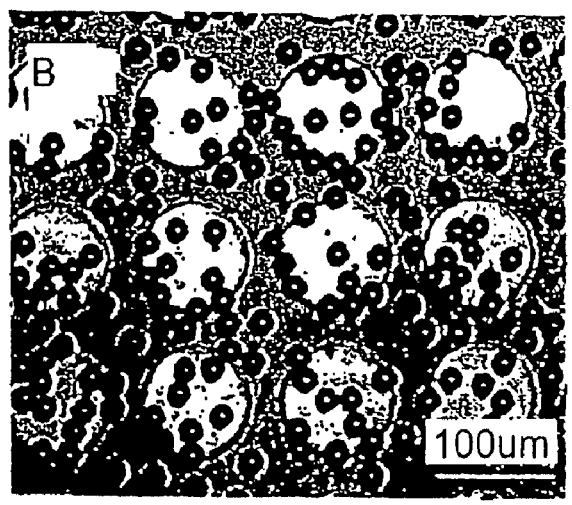
FIG. 6b illustrates that after reversing the bias the same microspheres were dislodged from the surface of this electrode.

The results of patterning 20 μm diameter polystyrene spheres in deionized water are shown in FIG. 6, consisting of FIGS. 6a and 6b. FIG. 6a shows that the microspheres spheres were patterned within the dot areas of the electrode (the anode 11, as shown in FIG. 1) when +1 volt bias is applied. FIG. 6b illustrates that after reversing the bias to −2 V the same microspheres were dislodged from the surface of this electrode (and, indeed, adhere to neither electrode).

6. Applications of the Apparatus and Method of the Invention

The apparatus and method of the invention has application in cell-based biosensors, drug discovery, pharmacogenomics, functional genomics, high throughput phenotyping, and in-vitro biology (e.g., combinatorial cell culture, and signal transdunction mechanisms), or any application requiring massive parallelism with biological cells.

The apparatus and method of the invention has genomics applications in trapping genes in which expression levels are modified by specific compounds or conditions. For example, neural progenitor cells may be trapped, and individual clones established for generation of a library for use in large scale screening. The robust change in emission ratio permits use of the present invention to perform clonal selection by a flow-cytometry-based sorting procedure. In addition, the sensitivity of the assay permits study of the dose-response and kinetic behavior of gene transcription in a cell population using standard machinery for fluorometric analysis or fluorescence microscope digital imaging systems.

The manner in which the apparatus, and system, of the present invention might be used for biotechnological purposes is illustrated by discussion of this development of a neural progenitor cell library with random integration of a reporter gene throughout the genome (gene trapping) so as to identify genes that are differentially regulated after exposure to various compounds.

The use of a promoter trapping in cell lines must first be understood. Several strategies have been developed to trap genes in order to define their function in a living organism. See Evans et. al., 1997. This strategy randomly integrates a promoter-less reporter gene throughout the genome so that it is only transcribed when integration occurs in an active transcription unit. This is referred to as promoter trapping.

Figure 7A:
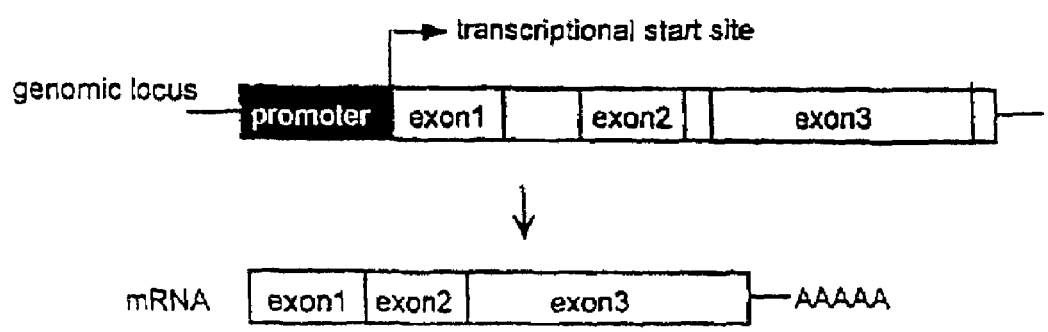
Figure 7B:
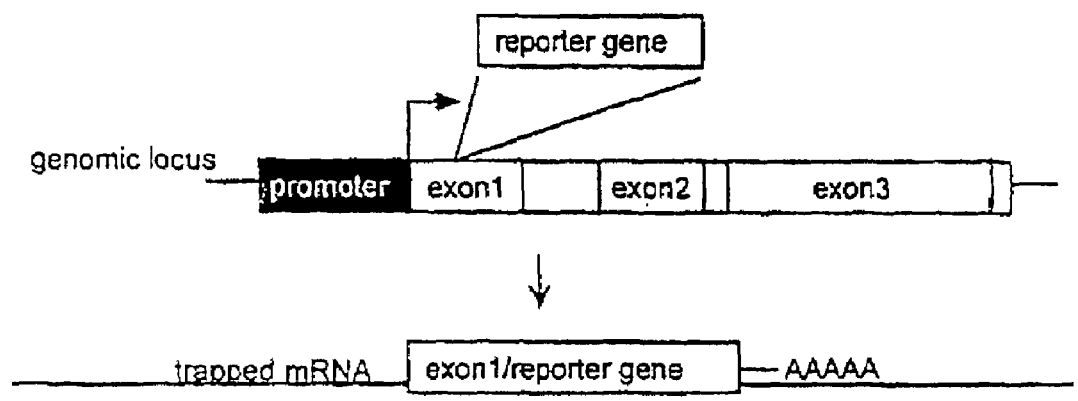
FIG. 7b shows the structure of the genomic locus after trapping.

The general scheme for gene trapping is illustrated in FIG. 7, consisting of FIGS. 7a and 7b. The components of a gene include the promoter, exons and introns, as shown in the grey tone box regions of FIG. 7a. Transcription results in an mRNA species as shown. The structure of the genomic locus after trapping is shown in FIG. 7b. The goal of the promoter trapping approach is to produce a transcript where the reporter construct has integrated into the 5' untranslated region or in a way to create an in-frame fusion, resulting in the appropriate expression of the reporter gene.

Another major obstacle has been the inability to study the expression of the reporter gene in real time in a living cell. All previous assays were based on the reporter genes chloramphenicol acetyltransferase, secreted alkaline phosphatase, p-galactosidase, and firefly luciferase. These methods either destroy the cell, lack resolution or are not quantitative. The technology of the present invention overcomes this problem as immediately next described.

A use of beta-lactamase and the apparatus and system of the present invention permits quantification of gene expression and the performance of clonal selection in real time in living cells. This is very useful.

Consider: correlation of gene expression with physiological responses and developmental fates can now be performed using a transcriptional assay that does not jeopardize cell survival. This technology allows for quantification of transcription and clonal selection of single living cells using, by way of example, beta-lactamase (p-lactamase) as a reporter and the apparatus and system of the present invention. As regards such use of beta-lactamase (p-lactamase), see, for example, Zlokamik et. al., 1998).

Figure 8:
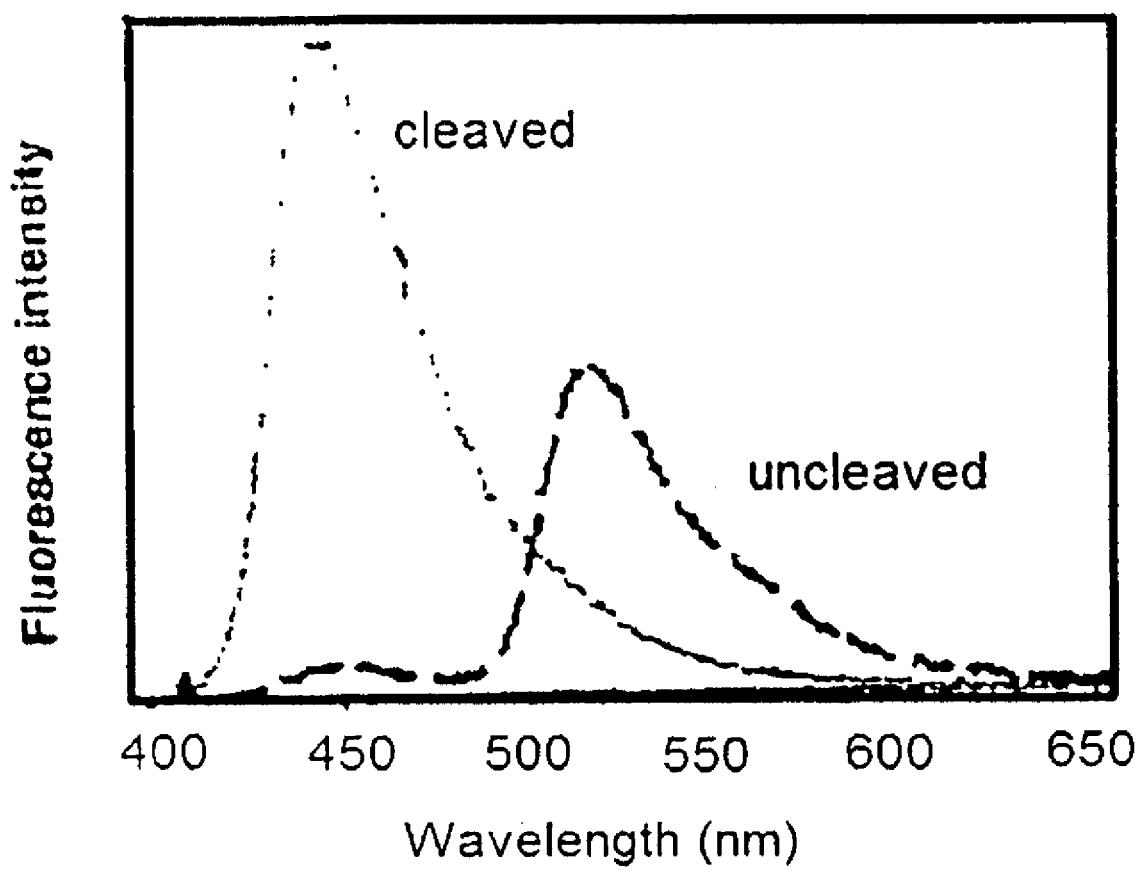
FIG. 8 shows the emission spectrum of the Cytoblast™ substrate before and after exposure to β-lactamase.

This nondestructive assay represents a major advance that it permits the use of promoter trapping in neural progenitor cells in order to study the influence of various compounds on gene expression. The combination of, for example, (i) beta-lactamase (p-lactamase) as a reporter and (ii) a substrate (commercially available as Cytoblast™) that is loaded intracellularly permits visualization of gene expression in single living mammalian cells. The β-lactamase enzyme catalyzes the hydrolysis of the substrate, thereby disrupting fluorescence resonance energy transfer (FRET) from the donor to the acceptor dye in the molecule. This wavelength shift is detectable by eye, flow cytometry, fluorimeter or color film in individual cells containing less than 100 β-lactamase molecules, and increases as more substrate is cleaved. See FIG. 8 showing the emission spectrum of the Cytoblast™ substrate before and after exposure to β-lactamase. Shown is the emission spectrum of cleaved (line on the left) or un-cleaved (dashed line on the right) substrate. The fluorescence intensity is plotted on the Y-axis and the wavelength on the X-axis.

This scheme can be used to trap genes whose expression levels are modified by specific compounds or conditions in neural progenitor cells, and to establish individual clones for generation of a library for large scale screening. The apparatus and system of the present invention simply permits that the assay process should be accomplished on a great number of cells in parallel at the same time.

The robust change in emission ratio permits use the (i) β-lactamase and the (ii) Cytoblast™ substrate, technology to perform clonal selection by flow cytometry based sorting procedure. In addition, the sensitivity of the assay permits study of the dose-response and kinetic behavior of gene transcription in the cell population using standard machinery for fluorometric analysis or fluorescence microscope digital imaging systems.

In a typical assay cells should first be electrophoretically arrayed into single cell islands without exposure to mechanical forces introduced by cytometry. A soluble stimulus would be introduced to the chamber, e.g., a hormone or differentiation factor. A fluorescent reporter system would preferably be used to visualize cellular response, e.g., gene expression dynamically in each cell. Cellular response would be correlated to array positions, e.g., row 3, column 4. Cells can be clonally expanded and characterized in situ or captured with optical tweezers or micromanipulators. Array position permits correlation of cellular responses with subsequent molecular characterizations.

In summary, transcriptional readouts are versatile screens for assessing mechanisms of toxicity because most signaling pathways, result in expression or repression of specific response elements and genes. Steps in disease progression likewise involve modulation of expression patterns, which can be monitored by transcriptional reporters even if the disease-causing mechanisms are not yet understood. Using the combination of neural progenitor cells and the β-lactamase reporter system facilitate this study by permitting visualization and quantification of changes in gene expression in living cells. Use of the apparatus and system of the present invention permits the system, and the assay, to be performed efficiently.

7. Recapitulation, and Conclusions

In accordance with the present invention, an apparatus with two parallel plates electrodes has been used in an electrochemical system to form microsphere and cellular micro arrays for drug screening and tissue engineering applications. In accordance with the invention multiple- or single-cell micro arrays have been formed by altering electrode size and a surrounding non-adhesive domain, such as may be formed from, inter alia, agarose.

A simple theoretical model serving to compute a force balance on spherical objects suffices to substantially explain observed behaviors. This model predicts that the voltage required for the disassembly of small objects, nominally polystyrene microbeads, is substantially higher than the voltage required for assembly. The difference arises due to the combined effects of gravity, frictional drag and van der Waals forces.

Furthermore, the apparatus and system of the present invention is extendible to the patterning of live mammalian cells by using low conductance physiologic buffers. Preliminary data with mouse 3T3 fibroblast demonstrates that cells maintain the ability to attach, spread and divide after exposure of up to 100 V/cm from the apparatus of the invention—much more than is required for operation.

The apparatus of the invention can serve as a powerful tool for high throughput biological screening.

In accordance with the preceding explanation, variations and adaptations of the electrokinetic apparatus and electrochemical system in accordance with the present invention will suggest themselves to practitioners of the electrical and chemical arts.

For example, the volume of the apparatus can be flushed with fluid containing reagents as the manipulated objects are selectively held to one electrode.

In accordance with these and other possible variations and adaptations of the present invention, the scope of the invention should be determined in accordance with the following claims, only, and not solely in accordance with that embodiment within which the invention has been taught.

What is claimed is:

1. A method of patterning cells in an assay, comprising
   providing cells within a fluid to an electrochemical apparatus that has electrodes separated by the fluid, one of the electrodes being made of a conductor and is patterned with an insulator selected from the group consisting of agarose, polymer and polydimethylsiloxane (PDMS) so as to leave patterned conducting regions of small size commensurate with the size of the cells, wherein the cells comprise a fluorescent indicator,
   providing a suitable electrical potential between the electrodes, to spatially pattern the cells
   introducing a soluble stimulus to the cells that are patterned into single cell islands; and
   measuring a cellular response to the soluble factor by measuring the fluorescent indicator.

2. The electrochemical apparatus according to claim 1, wherein the patterned electrode is nonadhesive.

3. The method according to claim 1, wherein the patterned electrode is the anode.

4. The method according to claim 1, wherein the at least one patterned-electrode is patterned in a regular array.

5. The method according to claim 1, wherein the at least one patterned electrode is patterned with regions suitably sized so as to capture, from a solution containing cells when an electrical potential is applied between the electrodes, a plurality of cells in each region.

6. The method according to claim 1, wherein the at least one patterned electrode is patterned with regions suitably sized so as to capture, from a solution containing cells when an electrical potential is applied between the electrodes, one cell in each region.

7. The method according to claim 1, wherein the at least one patterned electrode is so patterned with regions of size less than or equal to 100 μm.

8. The method of claim 1, wherein the insulator is selected from the group consisting of agarose, polymer and polydimethylsiloxane (PDMS) so as to leave patterned conducting regions of small size.

9. The method according to claim 1, wherein the fluid is water.

10. The method according to claim 1, wherein the electrodes of the electrochemical apparatus, plus the fluid, plus the applied electrical potential, are in combination effective to pattern cells.

11. The method according to claim 1, wherein the electrodes of the electrochemical apparatus, plus the fluid, plus the applied electrical potential, are in combination effective to pattern living cells.

12. The method according to claim 1, wherein the patterned cells are live.

13. The method according to claim 1 wherein the cells are so patterned into single cell islands.

14. The method according to claim 1, wherein the soluble stimulus is a hormone.

15. The method according to claim 1, wherein a fluorescent reporter is introduced to the cells so as to be used to visualize cellular response in presence of the stimulus.

16. The method according to claim 15 wherein the observed response is indicative of gene expression.

17. The method according to claim 15 wherein the observed response is so observed dynamically in real time as the cells respond to the stimulus.

18. The method according to claim 1 wherein the conductor is selected from the group consisting of silver and gold.

* * * * *